(12) United States Patent
Kordik et al.

(10) Patent No.: US 6,511,998 B2
(45) Date of Patent: Jan. 28, 2003

(54) PYRAZOLE CARBOXAMIDES USEFUL FOR THE TREATMENT OF OBESITY AND OTHER DISORDERS

(76) Inventors: Cheryl P. Kordik, 102 Summer Ridge Dr., Lansdale, PA (US) 19446; Timothy W. Lovenberg, 13252 Courtland Ter., San Diego, CA (US) 92130; Allen B. Reitz, 109 Greenbrier Rd., Lansdale, PA (US) 19446

(*) Notice: Subject to any disclaimer, the term of this patent is extended or adjusted under 35 U.S.C. 154(b) by 0 days.

(21) Appl. No.: 09/898,420

(22) Filed: Jul. 3, 2001

(65) Prior Publication Data

US 2002/0058816 A1 May 16, 2002

Related U.S. Application Data

(63) Continuation of application No. 09/563,190, filed on May 2, 2000, now Pat. No. 6,291,476.
(60) Provisional application No. 60/133,842, filed on May 12, 1999.

(51) Int. Cl.$^7$ .................. C07D 401/02; C07D 231/02; A61K 31/44
(52) U.S. Cl. .................. 514/341; 514/406; 546/275.4; 548/374.1
(58) Field of Search .................. 548/374.1; 514/406, 514/341; 546/275.4

(56) References Cited

U.S. PATENT DOCUMENTS

| | | | | |
|---|---|---|---|---|
| 4,950,668 A | * | 8/1990 | Okada et al. | 514/232.2 |
| 5,668,151 A | | 9/1997 | Poindexter et al. | 514/232.2 |
| 5,900,415 A | | 5/1999 | Peterson et al. | 514/232.2 |

FOREIGN PATENT DOCUMENTS

| | | |
|---|---|---|
| DE | 16 70 945 A | 3/1972 |
| EP | 41322 A1 * | 12/1981 |
| EP | 0 289 879 | 11/1988 |
| EP | 0 945 438 A1 | 9/1999 |
| EP | 0 945 439 A1 | 9/1999 |
| WO | WO 96/14307 | 5/1996 |
| WO | WO 96/16542 | 6/1996 |
| WO | 0 945 440 A1 | 6/1998 |
| WO | WO 98/25907 | 6/1998 |
| WO | WO 98/25908 | 6/1998 |
| WO | WO 98/27063 | 6/1998 |
| WO | WO 98/57951 A | 12/1998 |

OTHER PUBLICATIONS

Serradeil–Le Gal et al., SR120819A, an orally–active and selective neuropeptid Y Y1 receptor antagonist, FEBS Letters 362, Feb. 1995, 192–196.
Lundberg et al., Recent Developments with Neuropeptide Y Receptor Antagonists, TIPS Sep. 1996, vol. 17, 301–304.
Rudolf et al., The First Highly Potent and Selective Non–Peptide Neuropeptide Y Y1 Receptor Antagonist: BIBP3226, European J. of Pharmaceutical 1994, 271 R11–13.
Gehlert et al., Neuropeptide Y Antagonists: Clinical Promise and Recent Developments, Current Pharmaceutical Design, 1995, 1, 295–304.
Wright et al., 8–Amino–6 (Arylsulphonyl)–5–Nitroquinolines: Novel Nonpeptide Neuropeptide Y1 Receptor Antagonists, Bioorganic & Medical Chemistry Letters 1996 vo. 6, No. 15, 1809–1814.
R. Lan et al., "Structure–Activity Relationships of Pyrazole Derivatives as Cannabinoid Receptor Antagonists", J. Med. Chem 1999, 42(4), 769–776.

\* cited by examiner

Primary Examiner—Zinna Northington Davis

(57) ABSTRACT

Pyrazole carboxamide derivatives of the formula:

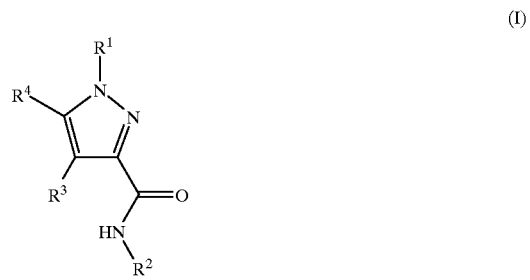

(I)

which are ligands for the neuropeptide Y, subtype 5 receptor, and pharmaceutical compositions containing a pyrazole carboxamide derivative as the active ingredient are described. The pyrazole carboxamides are useful in the treatment of disorders and diseases associated with the NPY receptor subtype Y5.

16 Claims, No Drawings

PYRAZOLE CARBOXAMIDES USEFUL FOR THE TREATMENT OF OBESITY AND OTHER DISORDERS

CROSS-REFERENCE TO RELATED APPLICATION

This application is a continuation of U.S. application Ser. No. 09/563,190, filed May 2, 2000, now issued as U.S. Pat. No. 6,291,476 B1, which claims priority from U.S. provisional application Ser. No. 60/133,842, filed May 12, 1999, the contents of which are hereby incorporated by reference.

FIELD OF THE INVENTION

This invention relates to a series of pyrazole carboxamide derivatives, pharmaceutical compositions containing them and their preparation use in the treatment of central nervous system disorders and affective conditions. More particularly, the compounds of the invention are ligands for the neuropeptide Y Y5 (NPY5) receptor, a receptor which is associated with a number of central nervous system disorders and affective conditions.

BACKGROUND OF THE INVENTION

Regulation and function of the mammalian central nervous system is governed by a series of interdependent receptors, neurons, neurotransmitters, and proteins. The neurons play a vital role in this system, for when externally or internally stimulated, they react by releasing neurotransmitters that bind to specific proteins. Common examples of endogenous small molecule neurotransmitters such as acetylcholine, adrenaline, norepinephrine, dopamine, serotonin, glutamate, and gamma-aminobutyric acid are well known, as are the specific receptors that recognize these compounds as ligands ("The Biochemical Basis of Neuropharmacology", Sixth Edition, Cooper, J. R.; Bloom, F. E.; Roth, R. H. Eds., Oxford University Press, New York, N.Y. 1991).

In addition to the endogenous small molecule neurotransmitters, there is increasing evidence that neuropeptides play an integral role in neuronal operations. Neuropeptides are now believed to be co-localized with perhaps more than one-half of the 100 billion neurons of the human central nervous system. In addition to humans, neuropeptides have been discovered in a number of animal species. In some instances the composition of these peptides is remarkably homogenous among species. This finding suggests that the function of neuropeptides is vital and has been impervious to evolutionary changes. Furthermore, neuropeptides, unlike small molecule neurotransmitters, are typically synthesized by the neuronal ribosome. In some cases, the active neuropeptides are produced as part of a larger protein which is enzymatically processed to yield the active substance. Based upon these differences, compared to small molecule neurotransmitters, neuropeptide-based strategies may offer novel therapies for CNS diseases and disorders. Specifically, agents that affect the binding of neuropeptides to their respective receptors or ameliorate responses that are mediated by neuropeptides are potential therapies for diseases associated with neuropeptides.

There are a number of afflictions that are associated with the complex interdependent system of receptors and ligands within the central nervous system; these include neurodegenerative diseases, affective disorders such as anxiety, depression, pain and schizophrenia, and affective conditions that include a metabolic component, namely obesity. Such conditions, disorders and diseases have been treated with small molecules and peptides which modulate neuronal responses to endogenous neurotransmitters.

One example of the class of neuropeptides is neuropeptide Y (NPY). NPY was first isolated from porcine brain (Tatemoto, K. et al. Nature 1982, 296, 659) and was shown to be structurally similar to other members of the pancreatic polypeptide (PP) family such as peptide YY, which is primarily synthesized by endocrine cells in the gut, and pancreatic polypeptide, which is synthesized by the pancreas. Neuropeptide Y is a single peptide protein that consists of thirty-six amino acids containing an amidated C-terminus. Like other members of the pancreatic polypeptide family, NPY has a distinctive conformation that consists of an N-terminal polyproline helical region and an amphiphilic α-helix joined by a characteristic PP-fold (Vladimir, S. et. Al. Biochemistry 1990, 20, 4509). Furthermore, NPY sequences from a number of animal species have been elucidated and all show a high degree of amino acid homology to the human protein (>94% in rat, dog, rabbit, pig, cow, sheep) (see Larhammar, D. in "The Biology of Neuropeptide Y and Related Peptides", Colmers, W. F. and Wahlestedt, C. Eds., Humana Press, Totowa, N.J. 1993).

Endogenous receptor proteins that bind NPY and related peptides as ligands have been identified and distinguished, and several such proteins have been cloned and expressed. Six different receptor subtypes [Y1, Y2, Y3, Y4(PP), Y5, Y6 (formerly designated as a Y5 receptor)] are recognized today based upon binding profile, pharmacology and/or composition if identity is known (Wahlestedt, C. et. al. Ann. NY Acad. Sci. 1990, 611, 7; Larhammar, D. et. al. J. Biol. Chem. 1992, 267, 10935; Wahlestedt, C. et. al. Regul. Pept. 1986, 13, 307; Fuhlendorff, J. U. et. al. Proc. Natl. Acad. Sci. USA 1990, 87, 182; Grundemar, L. et. al. J. Pharmacol. Exp. Ther. 1991, 258, 633; Laburthe, M. et. al. Endocrinology 1986, 118, 1910; Castan, I. et. al. Endocrinology 1992, 131, 1970; Gerald, C. et. al. Nature 1996, 382, 168; Weinberg, D. H. et. al. Journal of Biological Chemistry 1996, 271, 16435; Gehlert, D. et. al. Current Pharmaceutical Design 1995, 1, 295; Lundberg, J. M. et. al. Trends in Pharmaceutical Sciences 1996, 17, 301). Most and perhaps all NPY receptor proteins belong to the family of so-called G-protein coupled receptors (GPCRs). The neuropeptide Y5 receptor, a putative GPCR, is negatively coupled to cellular cyclic adenosine monophosphate (cAMP) levels via the action of adenylate cyclase (Gerald, C. et. al. Nature 1996, 382, 168; Gerald, C. et. al. PCT WO 96/16542). For example, NPY inhibits forskolin-stimulated cAMP production/levels in a neuroblastoma cell line. A Y5 ligand that mimics NPY in this fashion is an agonist whereas one that competitively reverses the NPY inhibition of forskolin-stimulated cAMP production is an antagonist.

Neuropeptide Y itself is the archetypal substrate for the NPY receptors and its binding can elicit a variety of pharmacological and biological effects in vitro and in vivo. When administered to the brain of live animals (intracerebroventricularly (icv) or into the amygdala), NPY produces anxiolytic effects in established animal models of anxiety such as the elevated plus-maze, Vogel punished drinking and Geller-Seifter's bar-pressing conflict paradigms (Heilig, M. et. al. Psychopharmacology 1989, 98, 524; Heilig, M. et. al. Reg. Peptides 1992, 41, 61; Heilig, M. et. al. Neuropsycho-pharmacology 1993, 8, 357). Thus compounds that mimic NPY are postulated to be useful for the treatment of anxiolytic disorders.

The immunoreactivity of neuropeptide Y is notably decreased in the cerebrospinal fluid of patients with major depression and those of suicide victims (Widdowson, P. S. et. al. *Journal of Neurochemistry* 1992, 59, 73), and rats treated with tricyclic antidepressants display significant increases of NPY relative to a control group (Heilig, M. et. al. *European Journal of Pharmacology* 1988, 147, 465). These findings suggest that an inadequate NPY response may play a role in some depressive illnesses, and that compounds that regulate the NPY-ergic system may be useful for the treatment of depression.

Neuropeptide Y improves memory and performance scores in animal models of learning (Flood, J. F. et. al. *Brain Research* 1987, 421, 280) and therefore may serve as a cognition enhancer for the treatment of neurodegenerative diseases such as Alzheimer's Disease (AD) as well as AIDS-related and senile dementia.

Elevated plasma levels of NPY are present in animals and humans experiencing episodes of high sympathetic nerve activity such as surgery, newborn delivery and hemorrhage (Morris, M. J. et. al. *Journal of Autonomic Nervous System* 1986, 17, 143). Thus chemical substances that alter the NPY-ergic system may be useful for alleviating the condition of stress.

Neuropeptide Y also mediates endocrine functions such as the release of luteinizing hormone (LH) in rodents (Kalra, S. P. et. al. *Frontiers in Neuroendrocrinology* 1992, 13, 1). Since LH is vital for mammalian ovulation, a compound that mimics the action of NPY could be useful for the treatment of infertility, particularly in women with so-called luteal phase defects.

Neuropeptide Y is a powerful stimulant of food intake; as little as one-billionth of a gram, when injected directly into the CNS, causes satiated rats to overeat (Clark, J. T. et. al. *Endocrinology* 1984, 115, 427; Levine, A. S. et. al. *Peptides* 1984, 5, 1025; Stanley, B. G. et. al. *Life Sci.* 1984, 35, 2635; Stanley, B. G. et. al. *Proc. Nat. Acad. Sci. USA* 1985, 82, 3940). Thus NPY is orexigenic in rodents but not anxiogenic when given intracerebroventricularly and so antagonism of neuropeptide receptors may be useful for the treatment of eating disorders such as obesity, binge eating, anorexia nervosa and bulimia nervosa.

In recent years, a variety of potent, structurally distinct small molecule Y1 antagonists has been discovered and developed (Hipskind, P. A. et. al. *Annu. Rep. Med. Chem.* 1996, 31, 1–10; Rudolf, K. et. al. *Eur. J. Pharmacol.* 1994, 271, R11; Serradeil-Le Gal, C. et. al. *FEBS Lett.* 1995, 362, 192; Wright, J. et. al. *Bioorg. Med. Chem. Lett.* 1996, 6, 1809; Poindexter, G. S. et. al. U.S. Pat. No. 5,668,151; Peterson, J. M. et. al. WO9614307 (1996)). However, despite claims of activity in rodent models of feeding, it is unclear if inhibition of a feeding response can be attributed to antagonism of the Y1 receptor.

Several landmark studies strongly suggest that an "atypical Y1" receptor and/or the Y5 receptor, rather than the classic Y1 receptor, is responsible for invoking NPY-stimulated food consumption in animals. It has been shown that the NPY fragment NPY2–36 is a potent inducer of feeding despite poor binding at the classic Y1 receptor (Stanley, B. G. et. al. *Peptides* 1992, 13, 581). Conversely, a potent and selective Y1 agonist has been reported to be inactive at stimulating feeding in animals (Kirby, D. A. et. al. *J. Med. Chem.* 1995, 38, 4579). More pertinent to the invention described herein, [D-Trp$^{32}$]NPY, a selective Y5 receptor activator has been reported to stimulate food intake when injected into the hypothalamus of rats (Gerald, C. et. al. *Nature* 1996, 382, 168). Since [D-Trp$^{32}$]NPY appears to be a full agonist of the Y5 receptor with no appreciable Y1 activity, the Y5 receptor is hypothesized to be responsible for the feeding response. Accordingly compounds that antagonize the Y5 receptor should be effective in inhibiting food intake, particularly that stimulated by NPY.

Also pertinent to the invention described herein, are aminopyrazoles that act as Y5 antagonists. In PCT WO 98/27063 and PCT WO 98/25908, certain aminopyrazoles are described as Y5 antagonists. In PCT WO 98/25907, (carbonylamino)pyrazole derivatives are likewise claimed as Y5 antagonists.

SUMMARY OF THE INVENTION

The present invention is directed to compounds of the formula (I):

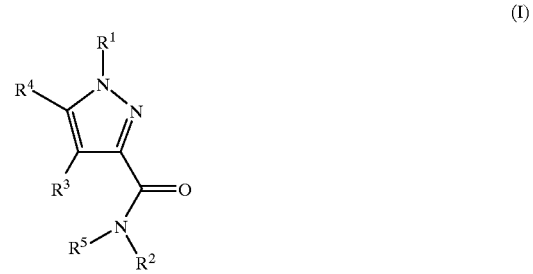

wherein
R$^1$ is selected from the group consisting Of C$_2$–C$_8$ alkyl, aryl, substituted aryl, arC$_1$–C$_8$ alkyl, substituted arC$_1$–C$_8$ alkyl, heteroaryl, substituted heteroaryl, C$_3$–C$_8$ cycloalkyl, heteroC$_3$–C$_8$cycloalkyl, fluorinated C$_1$–C$_8$ alkyl, cyanoC$_1$–C$_8$alkyl and hydroxyC$_1$–C$_8$alkyl; wherein the aryl, aralkyl or heteroaryl group is substituted with one or more substituents independently selected from halogen, C$_1$–C$_8$ alkyl, C$_1$–C$_8$ alkoxy, fluorinated C$_1$–C$_8$ alkyl, fluorinated C$_1$–C$_8$ alkoxy, nitro, amino, amido, N—C$_1$–C$_8$alkylamido, N,N-di(C$_1$–C$_8$alkyl)amido, C$_1$–C$_8$ alkylsulfonyl, sulfonamido, N—C$_1$–C$_8$alkylsulfonamido, N,N-di(C$_1$–C$_8$alky) sulfonamido, C$_1$–C$_8$alkylsulfonylamino, or C$_1$–C$_8$alkylcarbonylamino;

R$^2$ is selected from the group consisting of di(C$_1$–C$_6$ alkyl)amino-C$_1$–C$_6$ alkyl, unsubstituted or substituted heteroarylC$_0$–C$_6$ alkyl, unsubstituted or substituted heterocycloalkylC$_0$–C$_6$ alkyl, unsubstituted or substituted aryl, unsubstituted or substituted arC$_1$–C$_6$ alkyl, and unsubstituted or substituted C$_3$–C$_8$ cycloalkylC$_1$–C$_6$ alkyl where the substituent is arylsulfonamidoC$_1$–C$_6$ alkyl;

wherein
(a) the substituents on the aryl group are one or more substituents independently selected from the group consisting of halogen, nitro, amino, substituted amino where the substituents on the amino are one or two of C$_1$–C$_6$ alkyl or phenyl; fluorinated C$_1$–C$_6$ alkyl, fluorinated C$_1$–C$_6$ alkoxy, C$_1$–C$_6$ alkyl, substituted C$_1$–C$_6$ alkyl where the substituent on the alkyl is N—(C$_1$–C$_6$ alkyl)—N—(C$_3$–C$_8$ cycloalkyl) amino; C$_1$–C$_8$ alkoxy, arC$_1$–C$_8$ alkyl, arC$_1$–C$_8$ alkoxy, arylcarbonyl, phenyl, aminophenyl, C$_1$–C$_6$ alkylthio, substituted arylsulfonamido where the substituent on the arylsulfonamido is C$_1$–C$_6$ alkyl or C$_1$–C$_6$ alkoxy; heteroaryl, substituted heteroaryl where the substituent on the heteroaryl is C$_1$–C$_6$ alkyl, heterocycloalkyl and oxo;

(b) the substituents on the aralkyl group are one or more substituents independently selected from halogen or fluorinated $C_1$–$C_4$ alkyl;

(c) the substituents on the heterocycloalkyl group are one or more substituents independently selected from $C_1$–$C_6$ alkyl or ar$C_1$–$C_8$ alkyl;

(d) the substituents on the heteroaryl group are one or more substituents independently selected from oxo, $C_1$–$C_6$ alkyl or halogen;

$R^3$ is selected from the group consisting of hydrogen, halogen, $C_1$–$C_8$ alkyl, ar$C_1$–$C_8$ alkyl, heteroaryl$C_1$–$C_8$ alkyl, $C_1$–$C_8$ alkoxy, fluorinated $C_1$–$C_8$ alkyl, fluorinated $C_1$–$C_8$ alkoxy, amino$C_1$–$C_8$ alkyl and $C_1$–$C_8$ alkylamino$C_1$–$C_8$ alkyl; preferably, $R^3$ is hydrogen;

$R^4$ is selected from the group consisting of halogen, $C_1$–$C_8$ alkyl, ar$C_1$–$C_8$ alkyl, heteroaryl$C_1$–$C_8$ alkyl, fluorinated $C_1$–$C_8$ alkyl, amino$C_1$–$C_8$ alkyl and $C_1$–$C_8$ alkylamino$C_1$–$C_8$ alkyl; preferably, $R^4$ is $C_1$–$C_4$ alkyl;

$R^5$ is selected from the group consisting of hydrogen and $C_1$–$C_8$ alkyl; preferably, $R^5$ is hydrogen or $C_1$–$C_4$ alkyl provided that when $R^1$ is phenyl or benzyl, and $R^3$ is hydrogen, and $R^4$ is methyl, and $R^5$ is hydrogen, then $R^2$ is selected from di($C_1$–$C_6$ alkyl)amino$C_1$–$C_6$ alkyl, unsubstituted or substituted heteroaryl$C_0$–$C_6$ alkyl, unsubstituted or substituted heterocycloalkyl$C_0$–$C_6$ alkyl, substituted ar$C_1$–$C_6$ alkyl, unsubstituted or substituted $C_3$–$C_8$ cycloalkyl$C_1$–$C_6$ alkyl where the substituent is arylsulfonamido$C_1$–$C_6$ alkyl, and substituted aryl wherein the substituents on the aryl group are one or more substituents independently selected from the group consisting of halogen, nitro, amino, substituted amino where the substituents on the amino are one or two of $C_1$–$C_6$ alkyl or phenyl; fluorinated $C_1$–$C_6$ alkyl, fluorinated $C_1$–$C_6$ alkoxy, $C_1$–$C_6$ alkyl (provided that $R^2$ is not di($C_1$–$C_4$ alkyl)phenyl), substituted $C_1$–$C_6$ alkyl where the substituent on the alkyl is N—($C_1$–$C_6$alkyl)-N-($C_3$–$C_8$ cycloalkyl)amino; $C_1$–$C_8$ alkoxy, ar$C_1$–$C_8$ alkyl, ar$C_1$–$C_8$ alkoxy, phenyl, aminophenyl, $C_1$–$C_6$ alkylthio, substituted arylsulfonamido where the substituent on the arylsulfonamido is $C_1$–$C_6$ alkyl or $C_1$–$C_6$ alkoxy; heteroaryl, substituted heteroaryl where the substituent on the heteroaryl is $C_1$–$C_6$ alkyl; heterocycloalkyl and oxo;

and pharmaceutically acceptable salts thereof.

In a one embodiment of the invention are compounds of the formula (I) wherein $R^1$ is selected from the group consisting of phenyl, 3-tolyl, 3-trifluoromethylphenyl, 3,5-dichlorophenyl, 3-chlorophenyl, and 2-chloro-5-trifluoromethylphenyl;

$R^2$ is selected from the group consisting of 4-fluorophenyl, 3,5-dichlorophenyl, 2,3-dichlorophenyl, 2-(1-pyrrolyl) phenyl, 2-(aminophenyl)phenyl, 3-trifluoromethoxyphenyl, 2-methylthiophenyl, 3-methylphenyl, 2-methylphenyl, 2,6-difluorophenyl, 2,3,4-trifluorophenyl, 2,3,6-trifluorophenyl, 3-chlorophenyl, 3-bromophenyl, 3-iodophenyl, 3-chloro-5-fluorophenyl, 3-methoxy-5-trifluoromethylphenyl, 3-trifluoromethyl-4-fluorophenyl, 5,6,7,8-tetrahydronapthyl, 2-benzylphenyl, phenyl, 3-trifluoromethylphenyl, 5-isoquinolinyl, 2-(N-methylamino)phenyl, 1-napthyl, 5-quinolinyl, 5-(3-methyl)isoquinolinyl and 3-nitrophenyl;

$R^3$ is hydrogen;

$R^4$ is methyl;

$R^5$ is hydrogen;

and pharmaceutically acceptable salts thereof.

In a class of the invention are compound of the formula (I), wherein $R^1$ is selected from the group consisting of 3-trifluoromethylphenyl, 3,5-dichlorophenyl and 3-tolyl;

$R^2$ is selected from the group consisting of 3,5-dichlorophenyl, 2-(aminophenyl)-phenyl, 2,6-difluorophenyl, 2,3,6-trifluorophenyl, 5,6,7,8-tetrahydronapthyl, 2-benzylphenyl, 3-trifluoromethylphenyl, 5-isoquinolyl and 5-quinolinyl;

$R^3$ is hydrogen;

$R^4$ is methyl;

$R^5$ is hydrogen;

and pharmaceutically acceptable salts thereof.

Particularly preferred are compounds of the formula (I) wherein $R^1$ is 3-trifluoromethylphenyl; $R^2$ is selected from 3,5-dichlorophenyl or 5-isoquinolinyl; $R^3$ is hydrogen; $R^4$ is methyl; $R^5$ is hydrogen; and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention is a method of treating a condition mediated by the NPY Y5 receptor in a subject in need thereof comprising administering to the subject a therapeutically effective amount of any of the compounds or pharmaceutical compositions described above.

An example of the invention is a method for treating a condition selected from eating disorder, obesity, bulimia nervosa, diabetes, binge eating, anorexia nervosa, dyslipidimia, hypertension, memory loss, epileptic seizures, migraine, sleep disturbances, pain, sexual/reproductive disorders, depression, anxiety, cerebral hemorrhage, shock, congestive heart failure, nasal congestion or diarrhea in a subject in need thereof comprising administering to the subject an effective amount of any of the compounds or pharmaceutical compositions described above.

Further illustrating the invention is the use of a compound of formula I in the preparation of a medicament for treating conditions mediated by the NPY Y5 receptor.

DETAILED DESCRIPTION OF THE INVENTION

The present invention provides pyrazole carboxamide derivative compounds, useful as ligands of the neuropeptide Y, subtype 5 receptor. More particularly, the present invention is directed to compounds of the general formula (I):

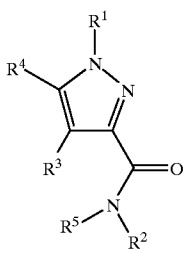

(I)

wherein

R¹, R², R³, R⁴ and R⁵ are as previously defined, and pharmaceutically acceptable salts thereof.

The compounds of the present invention may also be present in the form of pharmaceutically acceptable salts. For use in medicine, the salts of the compounds of this invention refer to non-toxic "pharmaceutically acceptable salts." Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid.

As used herein, unless otherwise noted, the term "halogen" shall include chlorine, fluorine, bromine and iodine.

As used herein, unless otherwise noted, the terms "alkyl" and "alkoxy" whether used alone or as part of a substituent group, include straight and branched chains having 1–8 carbon atoms, or any number within this range. For example, alkyl radicals include methyl, ethyl, n-propyl, isopropyl, n-butyl, isobutyl, sec-butyl, t-butyl, n-pentyl, 2-methyl-3-butyl, n-hexyl and the like. Alkoxy radicals are oxygen ethers formed from the previously described straight or branched chain alkyl groups. The terms "fluorinated alkyl" and "fluorinated alkoxy" as used herein refer to an alkyl or alkoxy group wherein one or more of the hydrogen atoms are replaced with a fluorine (e.g. trifluoromethyl, trifluoromethoxy).

As used herein, unless otherwise noted, "cycloalkyl" shall include saturated $C_3$–$C_8$ ring structures, preferably $C_5$–$C_8$ ring structures, for example cyclopropyl, cyclobutyl, cyclopentyl, cyclohexyl, cycloheptyl and the like.

As used herein, unless otherwise noted, "heterocycloalkyl" shall include saturated $C_5$–$C_6$ ring structures consisting of carbon and one to three heteroatoms (preferably one or two heteroatoms) selected from N, O or S (preferably N or O). Examples of suitable heterocycloalkyl groups include piperidinyl, morpholino, piperazinyl and the like.

As used herein, unless otherwise noted, "aryl" shall include aromatic groups such as: (a) phenyl, napthyl, fluorenyl, and the like; (b) partially unsaturated $C_9$–$C_{10}$ fused ring systems consisting of a phenyl fused to a five or six membered cycloalkyl (e.g. tetrahydronaphthyl, indanyl) or heterocycloalkyl (e.g. methylenedioxyphenyl, ethylenedioxyphenyl, tetrahydroisoquinolinyl) group; and (c) stable unsubstituted or substituted fourteen membered benzo-fused tricyclic ring system (e.g. anthraquinonyl).

As used herein, unless otherwise noted, "heteroaryl" shall denote: (a) a stable unsubstituted or substituted five or six membered monocyclic aromatic ring system; (b) a stable unsubstituted or substituted nine or ten membered benzo-fused heteroaromatic ring system which consists of carbon atoms and from one to six heteroatoms (preferably, one to four heteroatoms) selected from N, O or S; (c) a stable, unsubstituted or substituted nine or ten membered bicyclic fused heteroaromatic ring system which consists of carbon atoms and from one to six heteroatoms (preferably, one to four heteroatoms) selected from N, O or S (preferably N) or (d) a stable, unsubstituted or substituted fourteen membered benzo-fused tricyclic ring system which consists of carbon atoms and from one to six heteroatoms (preferably, one to three heteroatoms) selected from N, O or S (preferably O). The heteroaryl group may be attached at any heteroatom or carbon atom which results in the creation of a stable structure. Examples of suitable heteroaryl groups include, but are not limited to pyridyl, pyrazinyl, pyridazinyl, pirimidyl, thiophenyl, furanyl, imidazolyl, isoxazolyl, indolyl, indazolyl, isoindolyl, pyrazolyl, pyrrolyl, thiazolyl, thiadiazolyl, oxazolyl, triazolyl, tetrazolyl, purinyl, benzimidazolyl, benzofuranyl, benzothienyl, benzisoxazolyl, benzoxazolyl, benzopyrazolyl, indolyl, benzothiazolyl, benzothiadiazolyl, benzotriazolyl, quinolinyl or isoquinolinyl.

As used herein, unless otherwise noted, "aralkyl" shall mean any alkyl group substituted with an aryl group such as benzyl, phenylethyl and the like. Similarly, the term "aralkoxy" indicates an alkoxy group substituted with an aryl group. The term "aminoalkyl" refers to an alkyl group substituted with an amino group (i.e. -alkyl-$NH_2$). The term "alkylamino" refers to an amino group substituted with an alkyl group (i.e. —NH-alkyl). The term "dialkylamino" refers to an amino group which is disubstituted with alkyl groups wherein the alkyl group can be the same or different (i.e. —N-[alkyl]$_2$). Suitable alkyl and aryl groups are as defined above.

As used herein, unless otherwise noted, the term "amido" refers to —C(O)—$NH_2$. N-alkylamido and N,N-dialkylamido refers to —C—(O)—NH-alkyl and —C—(O)—N(alkyl)$_2$, respectively. Similarly, sulfonamido refers to —$SO_2$—$NH_2$.

Under standard nomenclature used throughout this disclosure, the terminal portion of the designated side chain is described first, followed by the adjacent functionality toward the point of attachment. Thus, for example, a "phenyl$C_1$–$C_6$ alkylamido$C_1$–$C_6$alkyl" substituent refers to a group of the formula

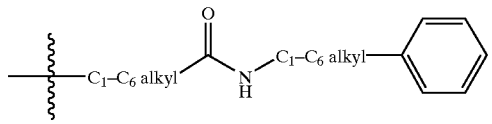

When a particular group (e.g. alkyl, aryl, heteroaryl) is substituted, that group may have one or more substituents (preferably, one to five, more preferably, one to three, most preferably, one to two substituents) independently selected from the list of substituents.

Whenever the term "alkyl" or "aryl" or either of their prefix roots appear in a name of a substituent (e.g. aralkyl, dialkylamino) it shall be interpreted as including those limitations given above for "alkyl" and "aryl". Designated numbers of carbon atoms (e.g. $C_1$–$C_6$) shall refer independently to the number of carbon atoms in an alkyl or cylcoalkyl moiety or to the alkyl portion of a larger substituent in which alkyl appears as its prefix root.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "subject" as used herein, refers to an animal, preferably mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The compounds of formula (I) that comprise this invention are generally referred to as pyrazole carboxamide derivatives, and are synthesized via the route outlined in Scheme 1; consisting of several sequential chemical operations that can be generalized as described below:

Formation of the pyrazole nucleus (ring closure)
Hydrolysis of the carboxylic ester to the carboxylic acid
Coupling of the acid to an appropriate amine In general, the synthesis of compounds of formula (I) consists of the steps of reacting a diketoester of formula (II) with an aryl or heteroaryl hydrazine to produce the 1,3,5-trisubstituted pyrazole of formula (III), further reacting the compound of formula (III) with a base to yield the corresponding carboxylic acid of formula (IV) and further reacting the carboxylic acid of formula (IV) with an aryl, heteroaryl or alkyl amine to afford the pyrazole carboxamide derivative of formula (I).

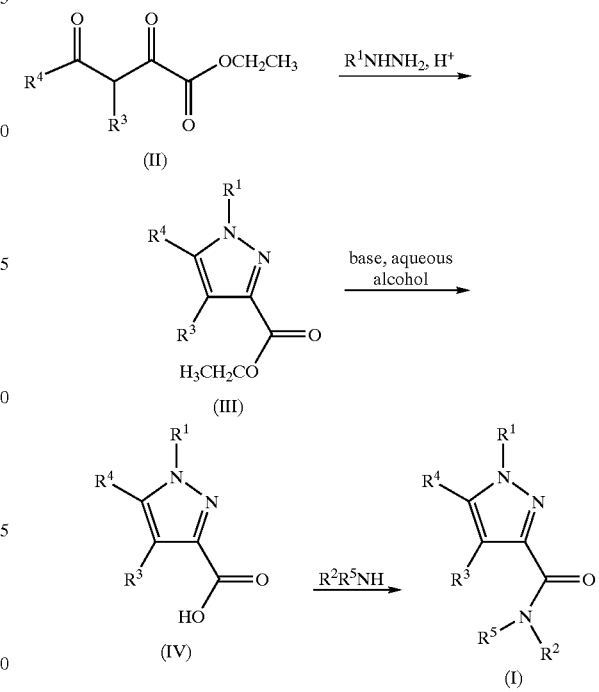

SCHEME 1

Specifically, a diketoester of the formula (II) is reacted with an aryl or heteroaryl hydrazine in the presence of an acid such as acetic acid, hydrochloric acid and the like, wherein the reaction solution is heated from ambient temperature to reflux, to afford the corresponding substituted pyrazoles of formula (III). The pyrazole of formula (III) is hydrolyzed in the presence of a base, such as sodium hydroxide, potassium carbonate and the like, in an aqueous alcoholic solvent, such as an aqueous methanolic solution, aqueous ethanolic solution and the like, wherein the reaction solution is heated from ambient temperature to reflux, to yield the pyrazole carboxylic acid of formula (IV). The pyrazole carboxylic acid of formula (IV) is coupled to an aryl, heteroaryl or alkyl amine (which may be primary or secondary) in the presence of a sterically hindered, non-nucleophilic amine, such as diisopropyl ethyl amine, triethyl amine and the like, and a coupling agent, such as O—(7-azabenzotriazol-1-yl)—N,N,N',N'-tetramethyluronium hexafluorophosphate (HATU), to provide the pyrazole carboxamides of formula (I) (Scheme 1).

The substituents $R^3$ and $R^4$ are varied by methods known to those skilled in the art, such as acylation of an appropriately substituted ketone of formula (V) with diethyl oxalate, in the presence of a base such as sodium hydride, sodium t-butoxide, lithium diisopropyl amide, and the like, to form the diketoester of formula (II), as shown in Scheme II.

SCHEME II

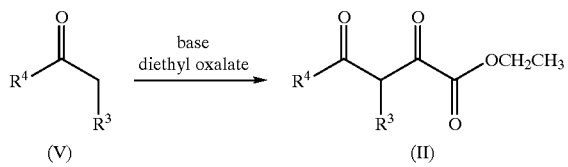

Alternately, the $R^3$ and $R^4$ substituents may be introduced via a process comprising the steps of acylating an appropriately substituted methyl ketone of formula (VI), with diethyl oxalate, in the presence of a base such as sodium hydride, sodium t-butoxide, lithium diisopropyl amide, and the like, to form the diketoester of formula (VII),

SCHEME III

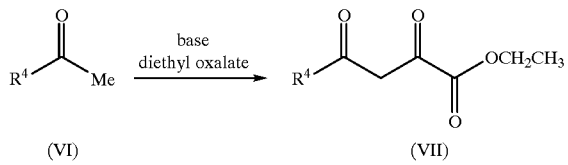

reacting the compound of formula (VII) (to introduce $R^3$) to form the compound of formula (II), via synthesis routes known to those skilled in the art, such as alkylation, electrophilic halogenation, displacement reactions of intermediate halo species, electrophilic amination and the like.

Those compounds of the present invention which contain a basic moiety can be converted to the corresponding acid addition salts by techniques known to those skilled in the art. Suitable acids which can be employed for this purpose include hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, or saccharin, and the like. In general, the acid addition salts can be prepared by reacting the free base of compounds of formula (I) with the acid and isolating the salt.

It is generally preferred that the respective product of each process step be separated from other components of the reaction mixture and then subjected to purification before its use as a starting material in a subsequent step. Separation techniques typically include evaporation, extraction, precipitation and filtration. Purification techniques typically include column chromatography (Still, W. C. et. al., J. Org. Chem. 1978, 43, 2921), thin-layer chromatography, crystallization and distillation. In those cases wherein the product is isolated as the acid addition salt, the free base is obtained by techniques known to those skilled in the art. The structures of the final products, intermediates and starting materials are confirmed by spectroscopic, spectrometric and analytical methods including nuclear magnetic resonance (NMR), mass spectrometry (MS) and liquid chromatography (HPLC).

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis,* John Wiley & Sons, 1991. The protecting groups may be removed at a convenient subsequent stage using methods known from the art.

As modulators of the NPY5 receptor, the compounds of Formula (I) are useful for treating feeding disorders such as obesity, binge eating, anorexia nervosa and bulimia nervosa, and abnormal conditions such as epilepsy, depression, anxiety and sexual/reproductive disorders in which modulation of the NPY5 receptor may be useful. The compounds compete with the endogenous ligands NPY and PYY and possibly non-endogenous ligands, and bind to the NPY5 receptor. In addition, the compounds demonstrate antagonist activity by antagonizing the action of NPY upon binding to the Y5 receptor.

The compounds described herein are ligands of the NPY5 receptor, but are not necessarily limited solely in their pharmacological or biological action due to binding to this or any neuropeptide, neurotransmitter or G-protein coupled receptor. For example, the described compounds may also undergo binding to dopamine or serotonin receptors. The compounds described herein are potentially useful in the regulation of metabolic and endocrine functions, particularly those associated with feeding, and as such, may be useful for the treatment of obesity. In addition, the compounds described herein are potentially useful for modulating other endocrine functions, particularly those controlled by the pituitary and hypothalamic glands, and therefore may be useful for the treatment of inovulation/infertility due to insufficient release of luteinizing hormone (LH).

The present invention further comprises pharmaceutical compositions containing one or more compounds of formula (I). The pharmaceutical composition of this invention alternately comprise a pharmaceutically acceptable carrier and one or more of the compounds of formula (I) described above. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.03 mg to 500 mg/kg (preferred 0.1–150 mg/kg) and may be given at a dosage of from about 0.1–300 mg/kg/day (preferred 1–150 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The present invention further provides a method of treatment of central nervous system disorders and affective conditions such as eating disorder, obesity, bulimia nervosa, diabetes, binge eating, anorexia nervosa, dyslipidimia, hypertension, memory loss, epileptic seizures, migraine, sleep disturbances, pain, sexual/reproductive disorders, depression, anxiety, cerebral hemorrhage, shock, congestive heart failure, nasal congestion or diarrhea.

The utility of the compounds to treat disorders of the central nervous system as described above, can be determined according to the procedures described herein. The present invention therefore provides a method of treating central nervous system disorders in a subject in need thereof which comprises administering any of the compounds as defined herein in a quantity effective to treat central nervous system disorders. The compound may be administered to a patient by any conventional route of administration, including, but not limited to, intravenous, oral, subcutaneous, intramuscular, intradermal and parenteral.

The method of treating central nervous system disorders described in the present invention may also be carried out using a pharmaceutical composition comprising any of the compounds as defined herein and a pharmaceutically acceptable carrier. The pharmaceutical composition may contain between about 0.01 mg and 500 mg, preferably about 5 to 150 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders of the central nervous system is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 500 mg/kg of body weight per day. Preferably, the range is from about 0.03 to about 300 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following example(s) describe the invention in greater detail and are intended to illustrate the invention, but not to limit it. All compounds were identified by a variety of methods including nuclear magnetic resonance spectroscopy, mass spectrometry and in some cases, infrared spectroscopy and elemental analysis. Nuclear magnetic resonance (300 MHz NMR) data is reported in parts per million downfield from tetramethylsilane. Mass spectra data is reported in mass/charge (m/z) units. Unless otherwise noted, the materials used in the example were obtained from readily available commercial sources or synthesized by standard methods known to those skilled in the art.

Abbreviations used in the instant specification, particularly the Schemes and Examples, are as follows:

| | |
|---|---|
| BSA = | Bovine Serum Albumin |
| Cmpd = | Compound |
| DIPEA = | Diisopropyl Ethyl Amine |
| EDTA = | Ethylene Diamine Tetraacetic Acid |
| EtOAc = | Ethyl acetate |
| HATU = | O-(7-Azabenzotriazol-1yl)-N,N,N",N"-Tetramethyl Uronium Hexafluorophosphate |
| HEPES = | 4-(2-hydroxyethyl)-1-Piperazine Ethane Sulfonic Acid |
| HPLC = | High Performance Liquid Chromatography |
| % Inh = | Percent Inhibition |
| MeOH = | Methanol |
| PBS = | Phosphate Buffered Saline |
| PEG = | Poly(Ethylene) Glycol |
| RT or rt = | Room temperature |

EXAMPLE 1

1-[(3-Trifluoromethyl)phenyl]-3-[N-5-(isoquinolinyl) carboxamide)]-5-methylpyrazole (110).

A. To a solution of ethyl 2,4-dioxovalerate (2.5 g, 16.0 mmol) in a 2:1 mixture of acetic acid and 2-methoxyethanol (48 mL) at room temperature in a 250 mL round-bottom flask fitted with a reflux condenser under nitrogen was added 3-(trifluoromethyl) phenylhydrazine (3.3 g, 19.0 mmol). The resultant solution was heated to reflux for 18 h. After cooling to room temperature, the volatiles were removed in vacuo and the residue was partitioned between EtOAc (200 mL) and 1N aq. HCl solution (200 mL). The layers were separated and the organic layer was washed with $H_2O$ (100 mL), dried over $Na_2SO_4$, and concentrated. The residue was purified by column chromatography on silica gel eluting with 5–10% EtOAc/hexanes provide the pyrazole ester III [$R_1$=3-(trifluoromethyl)phenyl, $R_3$=H, $R_4$=$CH_3$). $^1$H NMR (CDCl$_3$, 300 MHz) δ 1.42 (t, 3H, J=8.6 Hz), 2.40 (s, 3H), 4.42 (q, 2H, J=8.6 Hz). 6.78 (s, 1H), 7.65 (m, 3H), 7.79 (s 1H).

B. To a solution of pyrazole carboxylic ester III [R$_1$=3-(trifluoromethyl)phenyl; 2.19 g, 7.3 mmol] in a 3:1 MeOH/H$_2$O solution (150 mL) at room temperature in a 500 mL round-bottom flask fitted with a reflux condenser under nitrogen was added NaOH (440 mg, 11.0 mmol). The solution was heated to reflux for 18 h. The solution was allowed to cool to room temperature and was acidified to a pH of 2 with concentrated HCl. The solution was concentrated and the residue partitioned between CH$_2$Cl$_2$ (200 mL) and H$_2$O (200 mL). The layers were separated and the aqueous layer was extracted with 2×200 mL CH$_2$Cl$_2$. The combined organic layers were dried over Na$_2$SO$_4$ and concentrated to provide the acid IV [R$_1$=3-(trifluoromethyl)phenyl, R$_3$=H, R$_4$=CH$_3$]. $^1$H NMR (CDCl$_3$, 300 MHz) δ 2.41 (s, 3H), 6.84 (s, 1H), 7.70 (m, 3H), 7.78 (s, 1H).

C. To a solution of pyrazole carboxylic acid IV [R$_1$=3-(trifluoromethyl)phenyl; 100 mg, 0.37 mmol] in CH$_2$Cl$_2$ (5 mL) at room temperature was added DIPEA (0.13 mL) and HATU (142 mg, 0.37 mmol). The solution was allowed to stir at room temperature for 10 min. and then to it was added 5-aminoisoquinoline (59 mg, 0.41 mmol). The reaction mixture was allowed to stir at room temperature overnight, and then diluted with H$_2$O (10 mL) and extracted 3×10 mL of CH$_2$Cl$_2$. The organic layers were combined and washed with 2×10 mL 1N aq. HCl, 2×10 mL H$_2$O, dried over Na$_2$SO$_4$, and concentrated. The residue was purified by column chromatography eluting with 10% EtOAc/hexanes to provide the pyrazole carboxamide I [R$_1$=3-(trifluoromethyl)phenyl, R$_2$=5-quinolinyl, R$_3$=H, R$_4$=CH$_3$, Compound 110]. $^1$H NMR (CDCl$_3$, 300 MHz) δ 2.80 (s, 3H), 6.90 (s, 1H), 7.60–7.87 (m, 6H), 8,46 (d, 1H, J=8.5 Hz), 8.55 (d, 1H, J=6.8 Hz), 9.25 (s, 1H), 9.31 (s, 1H).

In a similar manner, all of the compounds of the present invention were been prepared by varying the necessary hydrazines and anilines.

EXAMPLE 2

As a specific embodiment of an oral composition, 100 mg of the compound 110 Of Example 1 is formulated with sufficient finely divided lactose to provide a total amount of 580 to 590 mg to fill a size O hard gel capsule.

EXAMPLE 3

In vitro Assays

NPY5 HTS Centrifugation Assay

The compounds described in this invention were evaluated for binding to the human neuropeptide Y5 receptor.

Stable Transfection

The human NPY5 receptor cDNA (Genbank Accession number U66275) was inserted into the vector pClneo (Invitrogen) and transfected into human embryonic kidney cells (HEK-293) via Calcium phosphate method (Cullen 1987). Stably transfected cells were selected with G-418 (600 ug/mL). Stably transfected cells served as the source for the membranes for the NPY5 receptor binding assay.

Membrane Preparation

PY5-transfected HEK293 cells were grown to confluence in 150 cm$^2$ culture dishes. Cells were washed once with phosphate-buffered saline (Gibco Cat# 14040-133). Cells were then incubated in phosphate-buffered saline without Calcium and without Magnesium, supplemented with 2 mM EDTA. Cells were incubated for 10 minutes at room temperature and the cells were collected by repetitive pipeting. Cells were formed into pellets and then frozen at −80 until needed. Frozen pellets were homogenized with a polytron at full speed for 12 seconds in a homogenization buffer (20 mM Tris HCl, 5 mM EDTA, pH 7.4). Homogenates were centrifuged for 5 minutes at 4C at 200 g. Supernatants were transferred to corex tubes and centrifuged for 25 minutes at 28,000 g. Pellets were re-suspended in Binding (20 mM HEPES, 10 mM NaCl, 0.22 mM KH$_2$PO$_4$, 1.3 mM CaCl$_2$, 0.8 mM MgSO$_4$, pH 7.4). Membranes were kept on ice until use.

A competition binding assay, known to those skilled in the art, was used in which the compounds of formula (I) compete with $^{125}$I-PYY for binding to cell membranes. In simple terms, the less $^{125}$I-PYY bound to the membranes implies that a compound is a good inhibitor (competitor). Bound $^{125}$I-PYY was determined by centrifugation of membranes, aspirating supernatant, washing away residual $^{125}$I-PYY and subsequently counting the bound sample in a g-counter.

Procedure for Radioligand Binding Assay

Compounds to be tested were prepared as 10× stocks in binding buffer and added first to assay tubes (RIA vials, Sarstedt). Twenty (20) µL of each 10× compound stock was pipeted into vials and 80 µL of $^{125}$I-PYY (NEN catalog number NEX240), which had been diluted to a concentration of 200 pM in 0.25% BSA in binding buffer, was added to the compound tubes (final concentration of $^{125}$I-PYY is 80 pM). To each tube was added 100 µL of membranes and the mixture was agitated by pipeting 2 times. Samples were incubated for 1 hr at room temperature. Aluminum cast plates (Sarstedt) containing the vials were then centrifuged 10 minutes at 3200 rpm in a Sorvall RT6000. Supernatant was then aspirated. To each vial 400 µL PBS was added and this was then aspirated again. Vials were then put in carrier polypropylene 12×75 tube and counted in gamma counter (Packard). Non-specific binding was determined in the presence of 300 nM NPY. Percent inhibition of $^{125}$I -PYY binding was calculated by subtracting non-specific binding from the test samples (compound (I)), taking these counts and dividing by total binding, and multiplying by 100. Inhibitory concentration values (IC$_{50}$) of compounds that showed appreciable inhibition of $^{125}$I-PYY binding were calculated by obtaining percent inhibition of $^{125}$I-PYY binding values at different concentrations of the test compound, and using a graphing program such as GraphPad Prism (San Diego, Calif.) the concentration of test compound that inhibits fifty-percent of $^{125}$I-PYY binding (Table 4) was calculated. These operations are known to those skilled in the art.

Mass Spectral Data and
Binding Affinities of Compounds (I) for the Human NPY Y5 Receptor
(expressed as % inhibition of $^{125}$I-PYY Binding or IC$_{50}$)

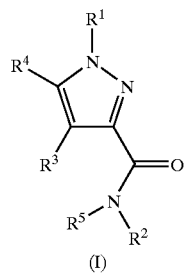

(I)

$R^3$ = hydrogen, $R^4$ = methyl, $R^5$ = hydrogen

| Cmpd # | R$^1$ | R$^2$ | % Inh NPY5r 3 μM | IC$_{50}$ HNPY5r | Mass (calcd) | Mass (obs) |
|---|---|---|---|---|---|---|
| 1 | 4-tolyl | 4-fluorophenyl | 36 | 8 μM | 309.34 | 310.3 |
| 2 | 4-tolyl | 3,5-dichlorophenyl | 67 | 3 μM | 360.24 | 360 |
| 3 | 4-tolyl | 4-methoxyphenyl | 7 | 20 μM | 321.38 | 322 |
| 4 | 4-tolyl | 4-chlorophenyl | 29 | | 325.60 | 326 |
| 5 | 3-trifluoromethyl phenyl | 4-fluorophenyl | 86 | 828 nM | 363.31 | 364 |
| 6 | 3-trifluoromethyl phenyl | 3,5-dichlorophenyl | 102 | 124 nM | 414.21 | 414.05 |
| 7 | 3-trifluoromethyl phenyl | 4-methoxyphenyl | 34 | | 375.35 | 376 |
| 8 | 3-trifluoromethyl phenyl | 4-(N-morpholino)-phenyl | 8 | | 430.43 | 431 |
| 9 | 3-trifluoromethyl phenyl | 4-chlorophenyl | 48 | | 379.77 | 380 |
| 10 | 3-trifluoromethyl phenyl | 2-(1-pyrrolyl) phenyl | 75 | 763 nM | 410.40 | 411 |
| 11 | 3-trifluoromethyl phenyl | ![piperidine-CH2-Ph] | 20 | | 442.48 | 443 |
| 12 | 3-trifluoromethyl | —N(piperazine)N—CH$_3$ | 30 | | 367.37 | 368 |
| 13 | 3-trifluoromethyl phenyl | —(CH$_2$)$_3$—N(2-methylpiperidine) | 22 | | 408.47 | 409 |
| 14 | 3-trifluoromethyl phenyl | —(CH$_2$)$_3$N(CH$_3$)$_2$ | 16 | | 354.37 | 355 |
| 15 | 3-trifluoromethyl phenyl | -2-(aminophenyl) phenyl | 91 | 267 nM | 436.44 | 437.14 |
| 16 | 3-trifluoromethyl phenyl | (2-methylphenyl)-benzimidazole | 0 | | 461.45 | 462.16 |
| 17 | 3-trifluoromethyl phenyl | 2-chlorophenyl | 2 | | 379.77 | 380.36 |

-continued

Mass Spectral Data and
Binding Affinities of Compounds (I) for the Human NPY Y5 Receptor
(expressed as % inhibition of $^{125}$I-PYY Binding or $IC_{50}$)

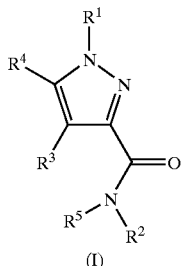

(I)

$R^3$ = hydrogen, $R^4$ = methyl, $R^5$ = hydrogen

| Cmpd # | $R^1$ | $R^2$ | % Inh NPY5r 3 μM | $IC_{50}$ HNPY5r | Mass (calcd) | Mass (obs) |
|---|---|---|---|---|---|---|
| 18 | 3-trifluoromethyl phenyl | 2-bromophenyl | 3 | | 424.22 | 425.35 |
| 19 | 3-trifluoromethyl phenyl | 2-iodophenyl | 10 | | 471.22 | 472.46 |
| 20 | 3-trifluoromethyl phenyl | 4-iodophenyl | 0 | | 471.22 | 472.27 |
| 21 | 3-trifluoromethyl phenyl | 3,4-dichlorophenyl | 47 | 1.5 μM | 414.21 | 415.28 |
| 22 | 3-trifluoromethyl phenyl | 3,5-dimethoxyphenyl | 48 | | 405.37 | 406.42 |
| 23 | 3-trifluoromethyl phenyl | 3-trifluoromethoxy phenyl | 83 | 431 nM | 429.32 | 430 |
| 24 | 3-trifluoromethyl phenyl | 4-trifluoromethoxy phenyl | 5 | | 429.32 | 430 |
| 25 | 3-trifluoromethyl phenyl | 2-methylthio phenyl | 63 | 881 nM | 391.41 | 392 |
| 26 | 3-trifluoromethyl phenyl | 2-methoxyphenyl | 6 | | 375.35 | 376 |
| 27 | 3-trifluoromethyl phenyl | 3-tolyl | 78 | 622 nM | 359.35 | 360 |
| 28 | 3-trifluoromethyl phenyl | 2-tolyl | 87 | 573 nM | 359.35 | 360 |
| 29 | 3-trifluoromethyl phenyl | 3,5-ditrifluoro methylphenyl | 79 | | 481.32 | 482 |
| 30 | 3-trifluoromethyl phenyl | 2,3-difluorophenyl | 83 | | 381.30 | 382 |
| 31 | 3-trifluoromethyl phenyl | 2,5-difluorophenyl | 25 | | 381.30 | 382 |
| 32 | 3-trifluoromethyl phenyl | 2,6-difluorophenyl | 95 | 233 nM | 381.30 | 382 |
| 33 | 3-trifluoromethyl phenyl | 3,4-difluorophenyl | 82 | | 381.30 | 382 |
| 34 | 3-trifluoromethyl phenyl | 2,3,4-trifluorophenyl | 87 | 885 nM | 399.29 | 400 |
| 35 | 3-trifluoromethyl phenyl | 2,4,5-trifluorophenyl | 0 | | 399.29 | 400 |
| 36 | 3-trifluoromethyl phenyl | 2,4,6-trifluorophenyl | 12 | | 399.29 | 400 |
| 37 | 3-trifluoromethyl phenyl | 2,3,6-trifluorophenyl | 96 | 229 nM | 399.29 | 400 |
| 38 | 3-trifluoromethyl phenyl | 2-fluorophenyl | 72 | | 363.31 | 364.09 |
| 39 | 3-trifluoromethyl phenyl | 3-chlorophenyl | 93 | 520 nM | 379.77 | 380.07 |
| 40 | 3-trifluoromethyl phenyl | 3-bromophenyl | 94 | 359 nM | 424.22 | 426.04 |
| 41 | 3-trifluoromethyl phenyl | 3-iodophenyl | 87 | 670 nM | 471.21 | 472.01 |
| 42 | 3-trifluoromethyl phenyl | 2,5-dibromophenyl | 5 | | 503.11 | 504 |
| 43 | 3-trifluoromethyl phenyl | 2,4-dibromophenyl | 13 | | 503.11 | 504 |
| 44 | 3-trifluoromethyl phenyl | 3-chloro-5-fluorophenyl | 95 | 516 nM | 397.76 | 398 |
| 45 | 3-trifluoromethyl phenyl | 2,5-dimethoxyphenyl | 37 | | 405.37 | 406.37 |

-continued

Mass Spectral Data and
Binding Affinities of Compounds (I) for the Human NPY Y5 Receptor
(expressed as % inhibition of $^{125}$I-PYY Binding or $IC_{50}$)

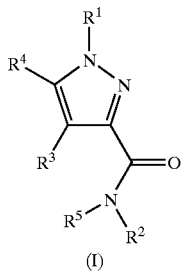

(I)

$R^3$ = hydrogen, $R^4$ = methyl, $R^5$ = hydrogen

| Cmpd # | $R^1$ | $R^2$ | % Inh NPY5r 3 μM | $IC_{50}$ HNPY5r | Mass (calcd) | Mass (obs) |
|---|---|---|---|---|---|---|
| 46 | 3-trifluoromethyl phenyl | 3-methoxy-5-trifluoromethyl phenyl | 93 | 346 nM | 443.34 | 444.40 |
| 47 | 3-trifluoromethyl phenyl | 3-trifluoromethyl-4-fluorophenyl | 90 | 593 nM | 431.30 | 431.17 |
| 48 | 3-trifluoromethyl phenyl | 3-trifluoromethyl phenyl | 78 | | 413.32 | 413.25 |
| 49 | 3-trifluoromethyl phenyl | 2,6-dichlorophenyl | 4 | | 414.21 | 415.22 |
| 50 | 3-trifluoromethyl phenyl | ![benzodioxole] | 30 | | 389.33 | 390.40 |
| 51 | 3-trifluoromethyl phenyl | ![benzodioxane] | 40 | | 403.36 | 404.41 |
| 52 | 3-trifluoromethyl phenyl | 2,4,6-trifluoro methylphenyl | 74 | | 387.40 | 388.36 |
| 53 | 3-trifluoromethyl phenyl | ![piperidinyl-methylphenyl] | 19 | | 428.45 | 429.20 |
| 54 | 3-trifluoromethyl phenyl | 2-biphenyl | 94 | | 421.42 | 422.14 |
| 55 | 3-trifluoromethyl phenyl | ![tetrahydronaphthyl] | 96 | 197 nM | 399.41 | 400.19 |
| 56 | 3-trifluoromethyl phenyl | 2-benzylphenyl | 93 | 292 nM | 435.45 | 436.18 |

-continued

Mass Spectral Data and
Binding Affinities of Compounds (I) for the Human NPY Y5 Receptor
(expressed as % inhibition of $^{125}$I-PYY Binding or IC$_{50}$)

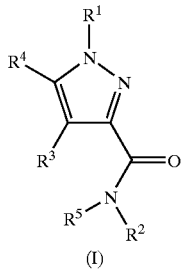

(I)

$R^3$ = hydrogen, $R^4$ = methyl, $R^5$ = hydrogen

| Cmpd # | $R^1$ | $R^2$ | % Inh NPY5r 3 μM | IC$_{50}$ HNPY5r | Mass (calcd) | Mass (obs) |
|---|---|---|---|---|---|---|
| 57 | 3-trifluoromethyl phenyl | (indanyl structure) | 59 | | 385.39 | 386.15 |
| 58 | 3-trifluoromethyl phenyl | 2-benzoylphenyl | 57 | | 449.43 | 450.15 |
| 59 | 3-trifluoromethyl phenyl | 3-benzyloxyphenyl | 35 | | 451.45 | 452.17 |
| 60 | 3-trifluoromethyl phenyl | 2,4,5-trichlorophenyl | 0 | | 448.66 | 449 |
| 61 | 4-trifluoromethyl phenyl | 4-fluorophenyl | 28 | | 363.31 | 364.1 |
| 62 | 4-trifluoromethyl phenyl | 4-chlorophenyl | 13 | | 379.77 | 380.1 |
| 63 | 4-trifluoromethyl phenyl | 2-(1-pyrrolyl) phenyl | 16 | | 410.40 | 411.1 |
| 64 | 4-trifluoromethyl phenyl | 4-methoxyphenyl | 8 | | 375.35 | 376.1 |
| 65 | 4-trifluoromethyl phenyl | 3,5-dichlorophenyl | 49 | | 414.22 | 414 |
| 66 | 4-trifluoromethyl phenyl | 4-tolyl | 60 | | 514.53 | 515.3 |
| 67 | benzyl | 4-fluoromethyl phenyl | 14 | | 309.34 | 310.1 |
| 68 | benzyl | 3,5-dichlorophenyl | 57 | | 360.24 | 360.0 |
| 69 | benzyl | 2-(1-pyrrolyl) phenyl | 17 | | 356.43 | 357.2 |
| 70 | benzyl | 4-chlorophenyl | 14 | | 325.80 | 326.1 |
| 71 | 3-trifluoromethyl phenyl | 2-pyridyl | 45 | | 346.31 | 347.11 |
| 72 | 3-trifluoromethyl phenyl | 3-pyridyl | 83 | | 346.31 | 347.11 |
| 73 | 3-trifluoromethyl phenyl | (imidazopyrimidinyl structure) | 16 | | 387.32 | 389.10 |
| 74 | 3-trifluoromethy phenyl | (methylpyrazinyl structure) | 30 | | 347.30 | 348.10 |
| 75 | 3-trifluoromethyl phenyl | (tolyl-NH-SO$_2$-tolyl structure) | 81 | | 514.53 | 515.13 |

-continued

Mass Spectral Data and
Binding Affinities of Compounds (I) for the Human NPY Y5 Receptor
(expressed as % inhibition of $^{125}$I-PYY Binding or IC$_{50}$)

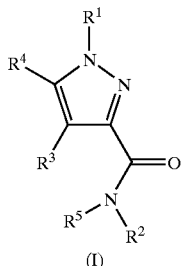

(I)

$R^3$ = hydrogen, $R^4$ = methyl, $R^5$ = hydrogen

| Cmpd # | R$^1$ | R$^2$ | % Inh NPY5r 3 μM | IC$_{50}$ HNPY5r | Mass (calcd) | Mass (obs) |
|---|---|---|---|---|---|---|
| 76 | 2-trifluoromethyl phenyl | 4-fluorophenyl | 13 | | 363.31 | 364.1 |
| 77 | 2-trifluoromethyl phenyl | 4-chloromethyl phenyl | 11 | | 379.77 | 380.1 |
| 78 | 2-trifluoromethyl phenyl | 2-(1-pyrrolyl) phenyl | 34 | | 410.40 | 411.1 |
| 79 | 2-trifluoromethyl phenyl | 3,5-dichlorophenyl | 22 | | 414.21 | 414.1 |
| 80 | 2-trifluoromethyl phenyl | 4-methoxyphenyl | 4 | | 375.35 | 376.2 |
| 81 | phenyl | 3,5-dichlorophenyl | 90 | 759 nM | 346.21 | 346.0 |
| 82 | phenyl | 4-chlorophenyl | 28 | | 311.77 | 312.0 |
| 83 | phenyl | 4-fluorophenyl | 39 | | 295.31 | 296.1 |
| 84 | phenyl | 4-methoxyphenyl | 12 | | 307.35 | 308.1 |
| 85 | phenyl | 2-(1-pyrrolyl) phenyl | 21 | | 342.40 | 343.1 |
| 86 | phenyl | Phenyl | 39 | | 277.32 | 278.1 |
| 87 | 3-trifluoromethyl phenyl | Phenyl | 84 | 1 μM | 345.32 | 346.1 |
| 88 | 3,5-dichlorophenyl | 4-fluorophenyl | 84 | 2 μM | 364.20 | 364.0 |
| 89 | 3,5-dichlorophenyl | 4-chlorophenyl | | 6 μM | 380.66 | 380.0 |
| 90 | 3,5-dichlorophenyl | 3,5-dichlorophenyl | | 1 μM | 415.11 | 415.9 |
| 91 | 3,5-dichlorophenyl | Phenyl | | 3 μM | 346.21 | 346.0 |
| 92 | 3,5-dichlorophenyl | 2-(1-pyrrolyl) phenyl | | 16 μM | 411.29 | 411.1 |
| 93 | 3-trifluoromethyl phenyl | 2,3-dichlorophenyl | | 1 μM | 414.21 | 414.1 |
| 94 | 3,5-dichlorophenyl | 2,3-dichlorophenyl | 0 | | 415.10 | 416 |
| 95 | 3,5-dichlorophenyl | 3,5-trifluoromethyl phenyl | | 5 μM | 482.21 | 481.8 |
| 96 | 3,5-dichlorophenyl | 3-trifluoromethyl phenyl | | 261 nM | 414.21 | 414.1 |
| 97 | 3-tolyl | 4-fluorophenyl | 68 | | 309.34 | 310.1 |
| 98 | 3-tolyl | 4-chlorophenyl | 57 | | 325.80 | 326.1 |
| 99 | 3-tolyl | 3,5-dichlorophenyl | 93 | 218 nM | 360.24 | 360.1 |
| 100 | 3-tolyl | Phenyl | 54 | | 291.35 | 292.1 |
| 101 | 3-tolyl | 2-(1-pyrrolyl) phenyl | 56 | | 356.43 | 357.2 |
| 102 | 3-trifluoromethyl phenyl | (6-fluoro-2-methylbenzothiazolyl) | 0 | | 420.39 | 421.0 |
| 103 | 3-trifluoromethyl phenyl | (2-methylindolyl) | | 5 μM | 460.46 | 461.1 |

-continued

Mass Spectral Data and
Binding Affinities of Compounds (I) for the Human NPY Y5 Receptor
(expressed as % inhibition of $^{125}$I-PYY Binding or $IC_{50}$)

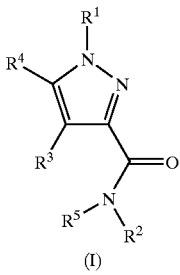

(I)

$R^3$ = hydrogen, $R^4$ = methyl, $R^5$ = hydrogen

| Cmpd # | $R^1$ | $R^2$ | % Inh NPY5r 3 μM | $IC_{50}$ HNPY5r | Mass (calcd) | Mass (obs) |
|---|---|---|---|---|---|---|
| 104 | 3-trifluoromethyl phenyl | 2-ethyl-benzimidazole | | 14 μM | 399.37 | 400.2 |
| 105 | 3-trifluoromethyl phenyl | 2-(4-methylphenyl)-6-methyl-benzothiazole | 0 | | 492.52 | 493.1 |
| 106 | 3-trifluoromethyl phenyl | 8-methylquinoline | 0 | | 396.37 | 397.2 |
| 107 | 3-trifluoromethyl phenyl | 7-methylquinoline | | 4 μM | 396.37 | 397.2 |
| 108 | 3-trifluoromethyl phenyl | 3-methylquinoline | | 13 μM | 396.37 | 397.2 |
| 109 | 3-trifluoromethyl phenyl | methylfluorene | | 6 μM | 433.43 | 434.1 |
| 110 | 3-trifluoromethyl phenyl | 5-methylisoquinoline | | 80 nM | 396.37 | 397.1 |
| 111 | 3-trifluoromethyl phenyl | 3-biphenyl | 33 | | 421.42 | 422.15 |

-continued

Mass Spectral Data and
Binding Affinities of Compounds (I) for the Human NPY Y5 Receptor
(expressed as % inhibition of $^{125}$I-PYY Binding or $IC_{50}$)

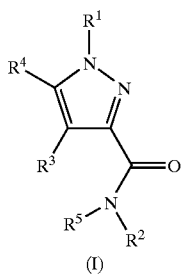

(I)

$R^3$ = hydrogen, $R^4$ = methyl, $R^5$ = hydrogen

| Cmpd # | $R^1$ | $R^2$ | % Inh NPY5r 3 μM | $IC_{50}$ HNPY5r | Mass (calcd) | Mass (obs) |
|---|---|---|---|---|---|---|
| 112 | 3-trifluoromethyl phenyl | H₃C–N(cyclohexyl)–CH₂–(2-methylphenyl) | 22 | | 470.53 | 471.4 |
| 113 | 3-trifluoromethyl phenyl | 2-(N-methyl amino)phenyl | 95 | 343 nM | 374.36 | 375.2 |
| 114 | 2-pyridyl | 4-fluorophenyl | 0 | | 296.30 | 297.11 |
| 115 | 2-pyridyl | 3,5-dichlorophenyl | 0 | | 347.20 | 347.03 |
| 116 | 2-pyridyl | 2-(1-pyrrolyl) phenyl | 5 | | 343.39 | 344.14 |
| 117 | 2-pyridyl | 2-(N-phenyl amino)phenyl | 18 | | 369.42 | 370.16 |
| 118 | 3-trifluoromethyl phenyl | 4-fluorobenzyl | 54 | | 377.34 | 378.12 |
| 119 | 3-trifluoromethyl phenyl | 3,5-dichlorobenzyl | 38 | | 428.24 | 428.07 |
| | | | | | 430.07 | |
| 120 | 3-trifluoromethyl phenyl | 3,5-trifluoromethyl benzyl | 31 | | 495.34 | 466.11 |
| 121 | 3-trifluoromethyl phenyl | 1-naphthyl | 95 | 356 nM | 395.38 | 396.15 |
| 122 | 3-trifluoromethyl phenyl | 2-naphthyl | 25 | | 395.38 | 396.14 |
| 123 | 3-trifluoromethyl phenyl | 5-methylindole | 36 | | 384.36 | 385.13 |
| 124 | 3-trifluoromethyl phenyl | 5-methylindazole | 31 | | 385.35 | 386.13 |
| 125 | 3-trifluoromethyl phenyl | 5-methylquinoline | 94 | 232 nM | 396.37 | 397.15 |
| 127 | 3-chlorophenyl | 4-fluorophenyl | 60 | | 329.76 | 330.1 |
| 128 | 3-chlorophenyl | Phenyl | 50 | | 311.77 | 312.1 |

-continued

Mass Spectral Data and
Binding Affinities of Compounds (I) for the Human NPY Y5 Receptor
(expressed as % inhibition of $^{125}$I-PYY Binding or IC$_{50}$)

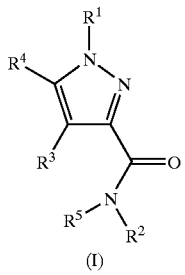

(I)

$R^3$ = hydrogen, $R^4$ = methyl, $R^5$ = hydrogen

| Cmpd # | R$^1$ | R$^2$ | % Inh NPY5r 3 μM | IC$_{50}$ HNPY5r | Mass (calcd) | Mass (obs) |
|---|---|---|---|---|---|---|
| 129 | 3-chlorophenyl | 5-methylisoquinolinyl | 90 | 450 nM | 362.81 | 363.1 |
| 130 | 3-chlorophenyl | 3,5-dichlorophenyl | 7 | | 380.66 | 382 |
| 131 | 3-chlorophenyl | 2-(1-pyrrolyl)phenyl | 29 | | 376.84 | 337.1 |
| 132 | 3-methoxyphenyl | 4-fluorophenyl | 38 | | 325.34 | 326.1 |
| 133 | 3-methoxyphenyl | Phenyl | 39 | | 307.35 | 308.1 |
| 134 | 3-methoxyphenyl | 5-methylisoquinolinyl | 82 | | 358.40 | 359.1 |
| 135 | 3-methoxyphenyl | 3,5-dichlorophenyl | 27 | | 376.24 | 376.0 |
| 136 | 3-methoxyphenyl | 2-(1-pyrrolyl)phenyl | 42 | | 372.43 | 373.1 |
| 137 | 3-fluorophenyl | 4-fluorophenyl | 44 | | 313.30 | 314.0 |
| 138 | 3-fluorophenyl | Phenyl | 42 | | 295.31 | 296.1 |
| 139 | 3-fluorophenyl | 5-methylisoquinolinyl | 79 | | 346.36 | 347.1 |
| 140 | 3-fluorophenyl | 3,5-dichlorophenyl | 29 | | 364.20 | 364.0 |
| 141 | 3-fluorophenyl | 2-(1-pyrrolyl)phenyl | 42 | | 360.39 | 361.1 |
| 142 | 3-chlorophenyl | 3-trifluoromethylphenyl | | 1.28 μM | 379.77 | 380.0 |
| 143 | 2-chloro-5-trifluoromethylphenyl | 4-fluorophenyl | 15 | | 397.58 | 398.1 |
| 144 | 2-chloro-5-trifluoromethylphenyl | Phenyl | 20 | | 379.77 | 380.1 |

-continued

Mass Spectral Data and
Binding Affinities of Compounds (I) for the Human NPY Y5 Receptor
(expressed as % inhibition of $^{125}$I-PYY Binding or $IC_{50}$)

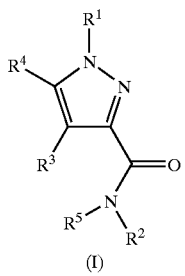

(I)

$R^3$ = hydrogen, $R^4$ = methyl, $R^5$ = hydrogen

| Cmpd # | $R^1$ | $R^2$ | % Inh NPY5r 3 μM | $IC_{50}$ HNPY5r | Mass (calcd) | Mass (obs) |
|---|---|---|---|---|---|---|
| 145 | 2-chloro-5-trifluoromethyl phenyl | 5-methylisoquinolinyl | | 324 nM | 430.81 | 431.4 |
| 146 | 2-chloro-5-trifluoromethyl phenyl | 3,5-dichlorophenyl | 30 | | 448.66 | 449.9 |
| 147 | 2-chloro-5-trifluoromethyl phenyl | 2-(1-pyrrolyl) phenyl | 21 | | 444.84 | 445.1 |
| 148 | 2-chloro-5-trifluoromethyl phenyl | 4-methylbenzothiadiazolyl | 3 | | 403.37 | 404.11 |
| 149 | 3-trifluoromethyl phenyl | 1-methylfluorenyl | 35 | | 435.45 | 434.3 |
| 150 | 3-trifluoromethyl phenyl | methyl-dibenzopyranonyl | 26 | | 465.43 | 464.0 |
| 151 | 3-trifluoromethyl phenyl | methyl-anthraquinonyl | 18 | | 477.44 | 477.44 |
| 152 | 3-trifluoromethyl phenyl | 5-methyl-3-methylisoquinolinyl | | 367 nM | 410.40 | 411.6 |

Mass Spectral Data and Binding Affinities of Compounds (I) for the Human NPY Y5 Receptor (expressed as % inhibition of $^{125}$I-PYY Binding or $IC_{50}$)

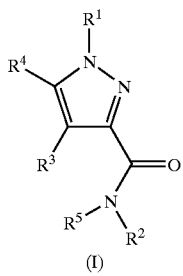

(I)

$R^3$ = hydrogen, $R^4$ = methyl, $R^5$ = hydrogen

| Cmpd # | $R^1$ | $R^2$ | % Inh NPY5r 3 µM | $IC_{50}$ HNPY5r | Mass (calcd) | Mass (obs) |
|---|---|---|---|---|---|---|
| 153 | 3-trifluoromethyl phenyl | ![5-methyl-1,2,3,4-tetrahydroisoquinoline] | 25 | | 400.40 | 401.4 |
| 154 | 3-trifluoromethyl phenyl | 3-nitrophenyl | | 1 µM | 390.32 | 391.11 |
| 155 | 3-trifluoromethyl phenyl | ![cyclohexylmethyl naphthalenesulfonamide] | 23 | | 584.66 | 585.0 |
| 156 | 3-trifluoromethyl phenyl | 3-aminophenyl | 53 | | 360.34 | 361.13 |
| 157 | 3-trifluoromethyl phenyl | 3-benzoylphenyl | | 2 µM | 449.43 | 450.1 |
| 158 | 3-trifluoromethyl phenyl | ![3-methylphenyl 4-methoxybenzenesulfonamide] | 52 | | 530.52 | 531.3 |

EXAMPLE 4

In vivo Assay

Rodent Feeding Model

Measurement of Food Intake in Food-Deprived Rats

Male Long-Evans rats (180–200 grams) were housed individually and were maintained on a once-a-day feeding schedule (i.e. 10 a.m. until 4 p.m.) for five days following quarantine to allow the animals to acclimate to feeding on powdered chow (#5002 PMI Certified Rodent Meal) during the allotted time. The chow was made available in an open jar, anchored in the cage by a wire, with a metal follower covering the food to minimize spillage. Water was available ad-libitum.

Animals were fasted for 18 hours prior to testing. At the end of the fasting period, animals were administered either compounds of the invention or vehicle. Vehicle and test compounds were administered either orally (5 mL/kg) 60 minutes prior to the experiment, or 30 minutes prior when given subcutaneously (1 mL/kg) or intraperitoneally (1 mL/kg). Compounds of the invention were administered orally as a suspension in aqueous 0.5% methylcellulose-0.4% Tween 80, or intraperitoneally as a solution or suspension in PEG 200; compound concentrations typically range from 1 mg/kg to 100 mg/kg, preferably from 10–30 mg/kg. Food intake was measured at 2, 4, and 6 hours after administration by weighing the special jar containing the food before the experiment and at the specified times. Upon completion of the experiment, all animals were given a one-week washout period before retesting.

Percent reduction of food consumption was calculated subtracting the grams of food consumed by the treated group from the grams of food consumed by the control group divided by the grams of food consumed by the control group, multiplied by 100.

$$\% \text{ change} = \frac{\text{Treatment} - \text{Vehicle}}{\text{Vehicle}} \times 100$$

A negative value indicated a reduction in food consumption and a positive value indicated an increase in food consumption.

| | | Food Consumption (grams) | | |
|---|---|---|---|---|
| Compound | Dose (mg/kg) (# rats) | 0–2 hrs (% change) | 0–6 hrs (% change) | 2–6 hrs (% change) |
| Vehicle | N = 16 | 8.44 g | 18.0 g | 9.56 g |
| PEG-2000 # 6 | 30 (i.p.) N = 16 | 4.5 g (−46.7%) | 12.10 g (−32.8%) | 7.63 g (−20.2%) |
| Vehicle | N = 8 | 10.38 g | 23.38 | 13.0 g |
| PEG-2000 # 110 | 30 (i.p.) N = 8 | 6.88 g (−33.73%) | 14.25 g (−39.04%) | 7.38 g (−43.3%) |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed:

1. A compound of the formula (I):

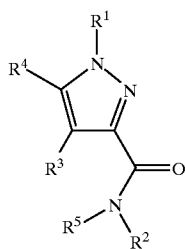

(I)

wherein
$R^1$ is selected from the group consisting of $C_2$–$C_8$ alkyl, aryl, substituted aryl, $arC_1$–$C_8$ alkyl, substituted $arC_1$–$C_8$ alkyl, heteroaryl, substituted heteroaryl, $C_3$–$C_8$ cycloalkyl, hetero$C_3$–$C_8$cycloalkyl, fluorinated $C_1$–$C_8$ alkyl, cyano$C_1$–$C_8$alkyl and hydroxy$C_1$–$C_8$alkyl; wherein the aryl, aralkyl or heteroaryl group is substituted with one or more substituents independently selected from halogen, $C_1$–$C_8$ alkyl, $C_1$–$C_8$ alkoxy, fluorinated $C_1$–$C_8$ alkyl, fluorinated $C_1$–$C_8$ alkoxy, nitro, amino, amido, N—$C_1$–$C_8$alkylamido, N,N-di($C_1$–$C_8$alkyl)amido, $C_1$–$C_8$ alkylsulfonyl, sulfonamido, N—$C_1$–$C_8$alkylsulfonamido, N,N-di($C_1$–$C_8$alky) sulfonamido, $C_1$–$C_8$alkylsulfonylamino, or $C_1$–$C_8$alkylcarbonylamino;

$R^2$ is selected from the group consisting of di($C_1$–$C_6$ alkyl)amino-$C_1$–$C_6$ alkyl, unsubstituted or substituted heteroaryl$C_1$–$C_6$ alkyl, unsubstituted or substituted heterocycloalkyl$C_1$–$C_6$ alkyl, unsubstituted or substituted aryl, unsubstituted or substituted ar$C_1$–$C_6$ alkyl, and unsubstituted or substituted $C_3$–$C_8$ cycloalkyl$C_1$–$C_6$ alkyl where the substituent is arylsulfonamido$C_1$–$C_6$ alkyl;

wherein
(a) the substituents on the aryl group are one or more substituents independently selected from the group consisting of halogen, nitro, amino, substituted amino where the substituents on the amino are one or two of $C_1$–$C_6$ alkyl or phenyl; fluorinated $C_1$–$C_6$ alkyl, fluorinated $C_1$–$C_6$ alkoxy, $C_1$–$C_6$ alkyl, substituted $C_1$–$C_6$ alkyl where the substituent on the alkyl is N—($C_1$–$C_6$ alkyl)—N—($C_3$–$C_8$ cycloalkyl) amino; $C_1$–$C_8$ alkoxy, ar$C_1$–$C_8$ alkyl, ar$C_1$–$C_8$ alkoxy, arylcarbonyl, phenyl, aminophenyl, $C_1$–$C_6$ alkylthio, substituted arylsulfonamido where the substituent on the arylsulfonamido is $C_1$–$C_6$ alkyl or $C_1$–$C_6$ alkoxy; heteroaryl, substituted heteroaryl where the substituent on the heteroaryl is $C_1$–$C_6$ alkyl, heterocycloalkyl and oxo;
(b) the substituents on the aralkyl group are one or more substituents independently selected from halogen or fluorinated $C_1$–$C_4$ alkyl;
(c) the substituents on the heterocycloalkyl group are one or more substituents independently selected from $C_1$–$C_6$ alkyl or ar$C_1$–$C_8$ alkyl;
(d) the substituents on the heteroaryl group are one or more substituents independently selected from oxo, $C_1$–$C_6$ alkyl or halogen;

$R^3$ is selected from the group consisting of hydrogen, halogen, $C_1$–$C_8$ alkyl, ar$C_1$–$C_8$ alkyl, heteroaryl$C_1$–$C_8$ alkyl, $C_1$–$C_8$ alkoxy, fluorinated $C_1$–$C_8$ alkyl, fluorinated $C_1$–$C_8$ alkoxy, amino$C_1$–$C_8$ alkyl and $C_1$–$C_8$ alkylamino$C_1$–$C_8$ alkyl;

$R^4$ is selected from the group consisting of halogen, $C_1$–$C_8$ alkyl, ar$C_1$–$C_8$ alkyl, heteroaryl$C_1$–$C_8$ alkyl, fluorinated $C_1$–$C_8$ alkyl, amino$C_1$–$C_8$ alkyl and $C_1$–$C_8$ alkylamino$C_1$–$C_8$ alkyl;

$R^5$ is selected from the group consisting of hydrogen and $C_1$–$C_8$ alkyl;

provided that when $R^1$ is phenyl or benzyl, and $R^3$ is hydrogen, and $R^4$ is methyl, and $R^5$ is hydrogen, then $R^2$ is selected from di($C_1$–$C_6$ alkyl)amino$C_1$–$C_6$ alkyl, unsubstituted or substituted heteroaryl$C_1$–$C_6$ alkyl, unsubstituted or substituted heterocycloalkyl$C_1$–$C_6$ alkyl, substituted ar$C_1$–$C_6$ alkyl, unsubstituted or substituted $C_3$–$C_8$ cycloalkyl$C_1$–$C_6$ alkyl where the substituent is arylsulfonamido$C_1$–$C_6$ alkyl, and substituted aryl wherein the substituents on the aryl group are one or more substituents independently selected from the group consisting of halogen, nitro, amino, substituted amino where the substituents on the amino are one or two of $C_1$–$C_6$ alkyl or phenyl; fluorinated $C_1$–$C_6$ alkyl, fluorinated $C_1$–$C_6$ alkoxy, $C_1$–$C_6$ alkyl (provided that $R^2$ is not di($C_1$–$C_4$ alkyl)phenyl), substituted $C_1$–$C_6$ alkyl where the substituent on the alkyl is N—($C_1$–$C_6$ alkyl)—N—($C_3$–$C_8$ cycloalkyl)amino; $C_1$–$C_8$ alkoxy, ar$C_1$–$C_8$ alkyl, ar$C_1$–$C_8$ alkoxy, phenyl, aminophenyl, $C_1$–$C_6$ alkylthio, substituted arylsulfonamido where the substituent on the arylsulfonamido is $C_1$–$C_6$ alkyl or $C_1$–$C_6$ alkoxy; heteroaryl, substituted heteroaryl where the substituent on the heteroaryl is $C_1$–$C_6$ alkyl; heterocycloalkyl and oxo;

and pharmaceutically acceptable salts thereof.

2. The compound of claim 1, wherein $R^5$ is hydrogen.

3. The compound of claim 1, wherein
$R^3$ is hydrogen, $R^4$ is $C_1$–$C_4$ alkyl, and $R^5$ is hydrogen or $C_1$–$C_4$ alkyl;
provided that when $R^1$ is phenyl or benzyl, and $R^4$ is methyl, then $R^2$ is selected from di($C_1$–$C_6$ alkyl) amino$C_1$–$C_6$ alkyl, unsubstituted or substituted heteroaryl$C_1$–$C_6$ alkyl, unsubstituted or substituted heterocycloalkyl$C_1$–$C_6$ alkyl, substituted ar$C_1$–$C_6$ alkyl, unsubstituted or substituted $C_3$–$C_8$ cycloalkyl$C_1$–$C_6$ alkyl where the substituent is arylsulfonamido$C_1$–$C_6$ alkyl, and substituted aryl wherein the substituents on the aryl group are one or more substituents independently selected from the group consisting of halogen, nitro, amino, substituted amino where the substituents on the amino are one or two of $C_1$–$C_6$ alkyl or phenyl; fluorinated $C_1$–$C_6$ alkyl, fluorinated $C_1$–$C_6$ alkoxy, $C_1$–$C_6$ alkyl (provided that $R^2$ is not dimethylphenyl), substituted $C_1$–$C_6$ alkyl where the substituent on the alkyl is N—($C_1$–$C_6$ alkyl)—N—($C_3$–$C_8$ cycloalkyl)amino; $C_1$–$C_8$ alkoxy, ar$C_1$–$C_8$ alkyl, ar$C_1$–$C_8$ alkoxy, phenyl, aminophenyl, $C_1$–$C_6$ alkylthio, substituted arylsulfonamido where the substituent on the arylsulfonamido is $C_1$–$C_6$ alkyl or $C_1$–$C_6$ alkoxy; heteroaryl, substituted heteroaryl where the substituent on the heteroaryl is $C_1$–$C_6$ alkyl; heterocycloalkyl and oxo;

and pharmaceutically acceptable salts thereof.

4. The compound of claim 2, wherein
$R^1$ is selected from the group consisting of pyridyl and substituted phenyl, wherein the phenyl is substituted with one to three substituents independently selected from $C_1$–$C_4$ alkyl, $C_1$–$C_4$ alkoxy, fluorinated $C_1$–$C_4$ alkyl, fluorinated $C_1$–$C_4$ alkoxy or halogen;
$R^2$ is selected from the group consisting of unsubstituted phenyl or substituted phenyl, where the substituents on the phenyl are independently selected from one to three of halogen, $C_1$–$C_4$ alkoxy, pyrrolyl, morpholino, aminophenyl, benzimidazolyl, fluorinated $C_1$–$C_4$ alkyl, fluorinated $C_1$–$C_4$ alkoxy, $C_1$L –$C_4$ alkylthio, nitro, $C_1$–$C_4$ alkyl, amino, $C_1$–$C_4$ alkylamino, phenyl amino, piperidinyl, phenyl, benzyl, benzoyl, benzyloxy, $C_1$–$C_4$ alkyl substituted benthiazolyl, $C_1$–$C_4$ alkyl substituted phenylsulfonamido, $C_1$–$C_4$ alkoxy substituted phenylsulfonamido or N—($C_1$–$C_4$ alkyl)—N—($C_3$–$C_6$ cycloalkyl)amino $C_1$–$C_4$ alkyl; unsubstituted or substituted benzyl, where the substituents on the benzyl are independently selected from one to three of halogen or fluorinated $C_1$–$C_4$ alkyl; napthyl, 3,4-methylenedioxyphenyl, 3,4-ethylenedioxyphenyl, 5,6,7,8-tetrahydronapthyl, indanyl, anthraquinonyl, indolylC–$C_4$ alkyl, fluorenyl, 3-(2-methyl pipiridinyl) propyl, di($C_1$–$C_4$ alkyl)amino$C_1$–$C_4$ alkyl, naphthylsulfonamido$C_1$–$C_4$ alkyl substituted cyclohexyl$C_1$–$C_4$ alkyl, 5-(3,4-benzocoumarinyl) and 5-(1,2,3,4-tetrahydroisoquinolinyl);
$R^3$ is selected from the group consisting of hydrogen, halogen, $C_1$–$C_4$ alkyl, $C_1$–$C_4$ alkoxy, fluorinated $C_1$–$C_4$ alkyl and fluorinated $C_1$–$C_4$ alkoxy;

$R^4$ is selected from the group consisting of hydrogen, $C_1$–$C_4$ alkyl and fluorinated $C_1$–$C_4$ alkyl;

and pharmaceutically acceptable salts thereof.

5. The compound of claim 3, wherein,
$R^1$ is selected from the group consisting of pyridyl and substituted phenyl, wherein the phenyl is substituted with one to three substituents independently selected from $C_1$–$C_4$ alkyl, $C_1$–$C_4$ alkoxy, fluorinated $C_1$–$C_4$ alkyl, fluorinated $C_1$–$C_4$ alkoxy or halogen;
$R^2$ is selected from the group consisting of unsubstituted phenyl or substituted phenyl, where the substituents on the phenyl are independently selected from one to three of halogen, $C_1$–$C_4$ alkoxy, pyrrolyl, morpholino, aminophenyl, benzimidazolyl, fluorinated $C_1$–$C_4$ alkyl, fluorinated $C_1$–$C_4$ alkoxy, $C_1$–$C_4$ alkylthio, nitro, $C_1$–$C_4$ alkyl, amino, $C_1$–$C_4$ alkylamino, phenyl amino, piperidinyl, phenyl, benzyl, benzoyl, benzyloxy, $C_1$–$C_4$ alkyl substituted benthiazolyl, $C_1$–$C_4$ alkyl substituted phenylsulfonamido, $C_1$–$C_4$ alkoxy substituted phenylsulfonamido or N—($C_1$–$C_4$ alkyl)—N—($C_3$–$C_6$ cycloalkyl)amino $C_1$–$C_4$ alkyl; unsubstituted or substituted benzyl, where the substituents on the benzyl are independently selected from one to three of halogen or fluorinated $C_1$–$C_4$ alkyl; napthyl, 3,4-methylenedioxyphenyl, 3,4-ethylenedioxyphenyl, 5,6,7,8-tetrahydronapthyl, indanyl, anthraquinonyl, indolyl$C_1$ –$C_4$ alkyl, fluorenyl, 3-(2-methyl pipiridinyl) propyl, di($C_1$–$C_4$ alkyl)amino$C_1$–$C_4$ alkyl, naphthylsulfonamido$C_1$ –$C_4$ alkyl substituted cyclohexyl$C_1$–$C_4$ alkyl, 5-(3,4-benzocoumarinyl) and 5-(1,2,3,4-tetrahydroisoquinolinyl);

$R^5$ is hydrogen;

and pharmaceutically acceptable salts thereof.

6. The compound of claim 5 wherein
$R^1$ is selected from the group consisting of phenyl, 3-tolyl, 3-trifluoromethylphenyl, 3,5-dichlorophenyl, 3-chlorophenyl, and 2-chloro-5-trifluoromethylphenyl;
$R^2$ is selected from the group consisting of 4-fluorophenyl, 3,5-dichlorophenyl, 2,3-dichlorophenyl, 2-(1-pyrrolyl) phenyl, 2-(aminophenyl)phenyl, 3-trifluoromethoxyphenyl, 2-methylthiophenyl, 3-tolyl, 2-tolyl, 2,6-difluorophenyl, 2,3,4-trifluorophenyl, 2,3,6-trifluorophenyl, 3-chlorophenyl, 3-bromophenyl, 3-iodophenyl, 3-chloro-5-fluorophenyl, 3-methoxy-5-trifluoromethylphenyl, 3-trifluoromethyl-4-fluorophenyl, 5,6,7,8-tetrahydronapthyl, 2-benzylphenyl, phenyl, 3-trifluoromethylphenyl, 2-(N-methylamino)phenyl, 1-naphthyl, and 3-nitrophenyl;

$R^4$ is methyl;

and pharmaceutically acceptable salts thereof.

7. The compound of claim 6, wherein
$R^1$ is selected from the group consisting of 3-trifluoromethylphenyl, 3,5-dichlorophenyl and 3-tolyl;
$R^2$ is selected from the group consisting of 3,5-dichlorophenyl, 2-(aminophenyl)-phenyl, 2,6-difluorophenyl, 2,3,6-trifluorophenyl, 5,6,7,8-tetrahydronapthyl, 2-benzylphenyl and 3-trifluoromethylphenyl;

and pharmaceutically acceptable salts thereof.

8. The compound of claim 7, wherein $R^1$ is 3-trifluoromethylphenyl and $R^2$ is 3,5-dichlorophenyl and pharmaceutically acceptable salts thereof.

9. A pharmaceutical composition comprising a compound of claim 1 and a pharmaceutically acceptable carrier.

10. A pharmaceutical composition made by mixing a compound of claim 1 and a pharmaceutically acceptable carrier.

11. A process for making a pharmaceutical composition comprising mixing a compound of claim 1 and a pharmaceutically acceptable carrier.

12. A method of treating a disorder mediated by the NPY Y5 receptor comprising administering to a subject in need of such treatment a therapeutically effective amount of a compound of claim 1.

13. The method of claim 12, wherein the therapeutically effective amount is between about 0.03 and about 300 mg/kg per day.

14. The method of claim 13, wherein the disorder is selected from an eating disorder, obesity, bulimia nervosa, diabetes, binge eating, anorexia nervosa, dyslipidimia, hypertension, memory loss, epileptic seizures, migraine, sleep disturbances, pain, sexual/reproductive disorders, depression, anxiety, cerebral hemorrhage, shock, congestive heart failure, nasal congestion or diarrhea.

15. A method of treating a disorder selected from an eating disorder, obesity, bulimia nervosa, diabetes, binge eating, anorexia nervosa, dyslipidimia, hypertension, memory loss, epileptic seizures, migraine, sleep disturbances, pain, sexual/reproductive disorders, depression, anxiety, cerebral hemorrhage, shock, congestive heart failure, nasal congestion or diarrhea in a subject in need thereof, comprising administering to the subject a therapeutically effective amount of a compound of claim 1.

16. The method of claim 15, wherein the therapeutically effective amount is between about 0.03 and about 300 mg/kg per day.

\* \* \* \* \*

UNITED STATES PATENT AND TRADEMARK OFFICE
CERTIFICATE OF CORRECTION

PATENT NO. : 6,511,998 B2
DATED : January 28, 2003
INVENTOR(S) : Cheryl P. Kordik et al.

It is certified that error appears in the above-identified patent and that said Letters Patent is hereby corrected as shown below:

<u>Column 41,</u>
Line 48, replace "$C_1L-C_4$" with -- $C_1-C_4$ --
Line 57, replace "napthyl" with -- naphthyl --
Line 60, replace "indolylC-$C_4$" with -- indolyl$C_1-C_4$ --

<u>Column 42,</u>
Line 25, replace "napthyl" with -- naphthyl --

Signed and Sealed this

Fourth Day of May, 2004

JON W. DUDAS
*Acting Director of the United States Patent and Trademark Office*